United States Patent
Meyer et al.

[11] Patent Number: 5,670,786
[45] Date of Patent: Sep. 23, 1997

[54] MULTIPLE WAVELENGTH LIGHT SOURCE

[75] Inventors: Ronald A. Meyer, San Dimas; Alexander Waluszko, Pasadena, both of Calif.

[73] Assignee: UVP, Inc., Opland, Calif.

[21] Appl. No.: 503,834

[22] Filed: Jul. 18, 1995

[51] Int. Cl.$^6$ .................... H01J 61/00; G01J 1/00
[52] U.S. Cl. .................... 250/494.1; 250/504 R; 362/802
[58] Field of Search .................... 250/504 R, 494.1; 606/17, 34, 42; 362/269, 260, 251, 276, 802, 295

[56] References Cited

U.S. PATENT DOCUMENTS

| | | | |
|---|---|---|---|
| 2,117,754 | 5/1938 | Bell | 88/24 |
| 2,484,159 | 10/1949 | Flynn | 362/802 |
| 2,725,461 | 11/1955 | Amour | 240/1.1 |
| 2,903,820 | 9/1959 | Bodell | 362/802 |
| 3,304,651 | 2/1967 | Deyerl | 362/802 |
| 4,000,407 | 12/1976 | Keller et al. | 240/103 R |
| 4,015,340 | 4/1977 | Treleven | 34/41 |
| 4,124,881 | 11/1978 | Haber et al. | 362/806 |
| 4,227,342 | 10/1980 | Knowles | 46/228 |
| 4,469,102 | 9/1984 | Fish | 128/395 |
| 4,480,294 | 10/1984 | Carboni | 362/251 |
| 4,657,655 | 4/1987 | Smoot et al. | 204/299 R |
| 4,683,379 | 7/1987 | Wolff | 250/493.1 |
| 4,701,146 | 10/1987 | Swenson | 362/802 |
| 4,712,014 | 12/1987 | Eich | 250/494 |
| 4,839,513 | 6/1989 | Wiijtsma | 250/504 R |
| 4,952,369 | 8/1990 | Belilos | 422/24 |
| 4,967,090 | 10/1990 | Schlitt | 250/504 R |
| 5,175,437 | 12/1992 | Waluszko | 250/504 R |
| 5,387,801 | 2/1995 | Gonzalez et al. | 250/504 R |

FOREIGN PATENT DOCUMENTS

| | | |
|---|---|---|
| 0 144 289 | 6/1985 | European Pat. Off. . |
| 1048606 | 11/1966 | United Kingdom . |
| 1161044 | 8/1969 | United Kingdom . |
| 1256639 | 12/1971 | United Kingdom . |
| 2075651 | 11/1981 | United Kingdom . |
| 2090396 | 7/1982 | United Kingdom . |
| 2205391 | 12/1988 | United Kingdom . |

*Primary Examiner*—Bruce Anderson
*Attorney, Agent, or Firm*—Lyon & Lyon LLP

[57] ABSTRACT

A transilluminator having two sets of tubes selectively providing light in the ultraviolet and visible ranges. The sets of tubes are arranged in two rows on opposite sides of a reflector in a housing having windows with lenses in opposite sides. The two sets of tubes have separate circuits sharing a common ON/OFF switch and a mercury switch mounted to the housing. With the device on, the orientation of the housing determines which of the two sets of tubes is on and which is off. Two sets of mounts to stably retain the housing on a planar surface are arranged on the opposite sides so that the housing may be positioned and used in two orientations. In either orientation, the upwardly facing lamps are energized while the downwardly facing lamps are turned off.

14 Claims, 5 Drawing Sheets

MULTIPLE WAVELENGTH LIGHT SOURCE

BACKGROUND OF THE INVENTION

The field of the present invention is lighting apparatus providing selected wavelengths of light.

Ultraviolet light is electromagnetic radiation in the region of the spectrum located between X-rays and visible light. It is divided into three principal ranges: (1) UV-A, or longwave, (2) UV-B, or mid-range, and (3) UV-C, or shortwave. For each of these UV ranges, specific applications have been developed for its use and new applications are continuously being developed.

To obtain a desired ultraviolet wavelength, the fluorescent tube is most commonly used. The fluorescent tube is an electric discharge device that uses a low pressure mercury vapor arc to generate ultraviolet energy. The ultraviolet energy released in typical, commercially available fluorescent tubes is primarily at the wavelength of about 254 nanometers. In general, this ultraviolet energy is converted into other ultraviolet wavelengths by the use of phosphors which have the ability to absorb the ultraviolet energy and re-radiate it in other wavelengths. For example, longwave ultraviolet of about 365 nanometers and mid-range ultraviolet of about 300 nanometers are created by coating the inside of the fluorescent tubes with the proper phosphor(s) which converts the shortwave ultraviolet. The envelope of the tube is also typically made of a glass that inhibits the passage of the shortwave ultraviolet. To obtain a shortwave ultraviolet tube, a special glass which transmits about 254 nanometers is generally used, and no phosphor is required.

A common tool of those engaged in DNA research is the ultraviolet transilluminator. These devices provide up to three ultraviolet light sources to irradiate and/or visualize DNA patterns contained in gel matrices. Most commonly, transilluminators comprise a single set of ultraviolet lamps emitting one selected wavelength. In many circumstances, more than one wavelength is desired. Thus, it is common to use multiple such units in this work or units with multiple filters on the working surface. At times, it may also be of value to employ a white light or specific spectral selections in the visual range such as, for example, the 420 nm and the 480 nm regions.

A conventional transilluminator having a single UV wavelength is disclosed in U.S. Pat. No. 4,657,655, incorporated herein by reference. An ultraviolet light apparatus having multiple wavelengths accomplished by rotation of a tube mounting mechanism is disclosed in U.S. Pat. No. 5,175,437, incorporated herein by reference. Another ultraviolet light apparatus having multiple wavelengths generated by an arrangement of three sets of tubes appropriately placed behind a lens is disclosed in U.S. Pat. No. 5,387,801, incorporated herein by reference.

SUMMARY OF THE INVENTION

The present invention is directed to a multiple wavelength light source having at least one lens on each of opposed sides of a housing with each lens capable of radiating different spectra in combination with a light source within the housing.

In a first and separate aspect of the present invention, the multiple wavelength light source includes mounts on both of the opposed sides of the housing. These stably support the housing on a planar surface with the opposite side facing upwardly to provide radiation of the selected spectra of light from the lens on that side. This provides a convenient source of two light box surfaces through a flipping of the housing.

In a second and separate aspect of the present invention, the multiple wavelength light source includes circuits selectively energizing the light source. The circuits jointly include a gravity switch mounted to move with the housing to alternatively open the circuits. This provides for alternatively and automatically energizing and turning off lights on opposed sides of the housing. The switch may be a mercury switch mounted to the housing. An ON/OFF switch for the unit may also be provided which closes both circuits simultaneously.

In a third and separate aspect of the present invention, the multiple wavelength light source includes radiating ultraviolet light from the first lens and radiating a second selected spectra of light from the second lens which is different from the light radiated from the first lens. The light from the second lens may be white light. This arrangement has particular applicability for convenient use for transillumination work requiring treatment by a selected ultraviolet range and illumination of the work in the visual range.

In yet another and separate aspect of the present invention, certain of the foregoing aspects may be combined to provide cooperative features for a more useful and convenient transilluminator design.

Accordingly, it is an object of the present invention to provide a convenient and improved multiple wavelength light source. Other and further objects and advantages will appear hereinafter.

DETAILED DESCRIPTION OF THE PREFERRED EMBODIMENT

Figure 1:
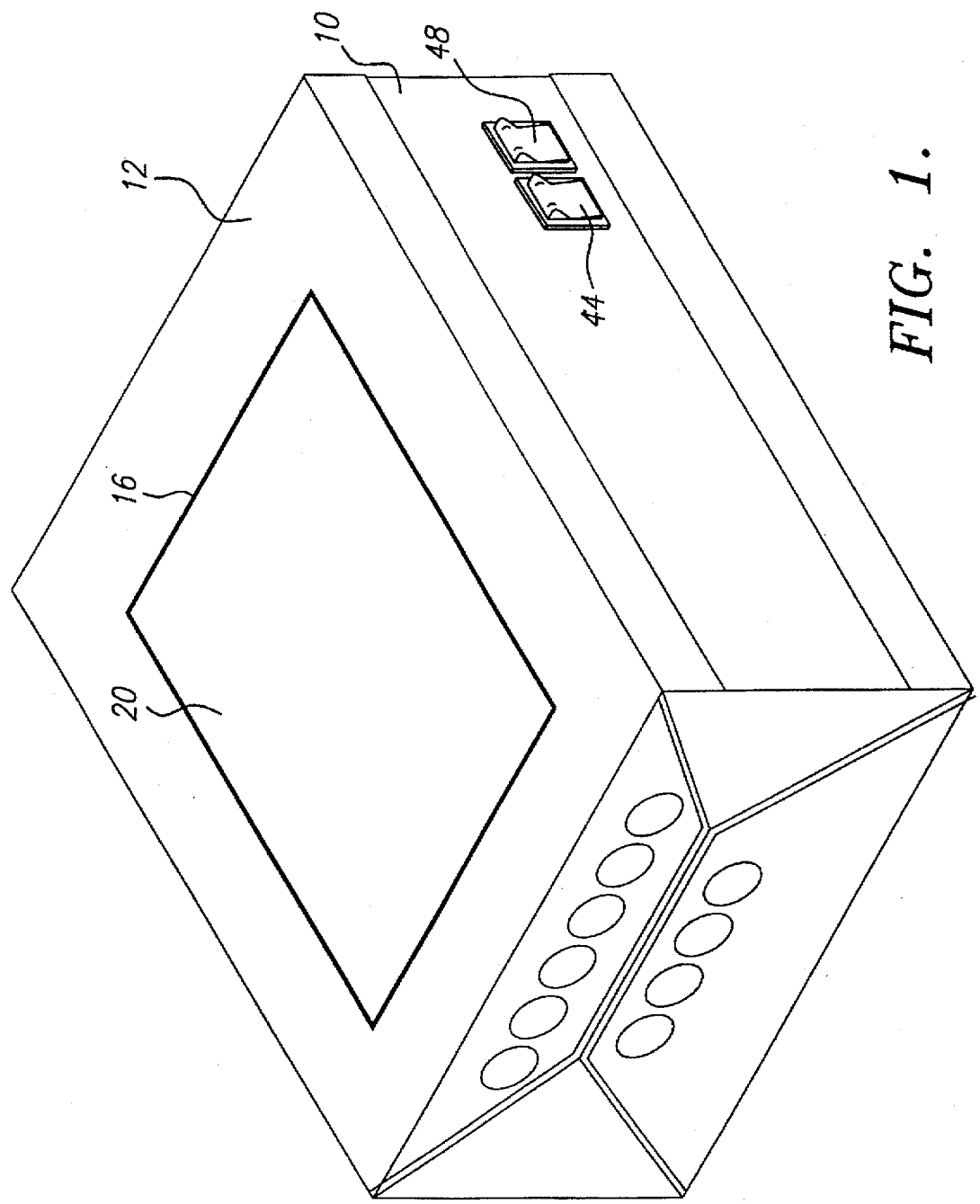
FIG. 1 is a perspective view of a transilluminator.
Figure 2:
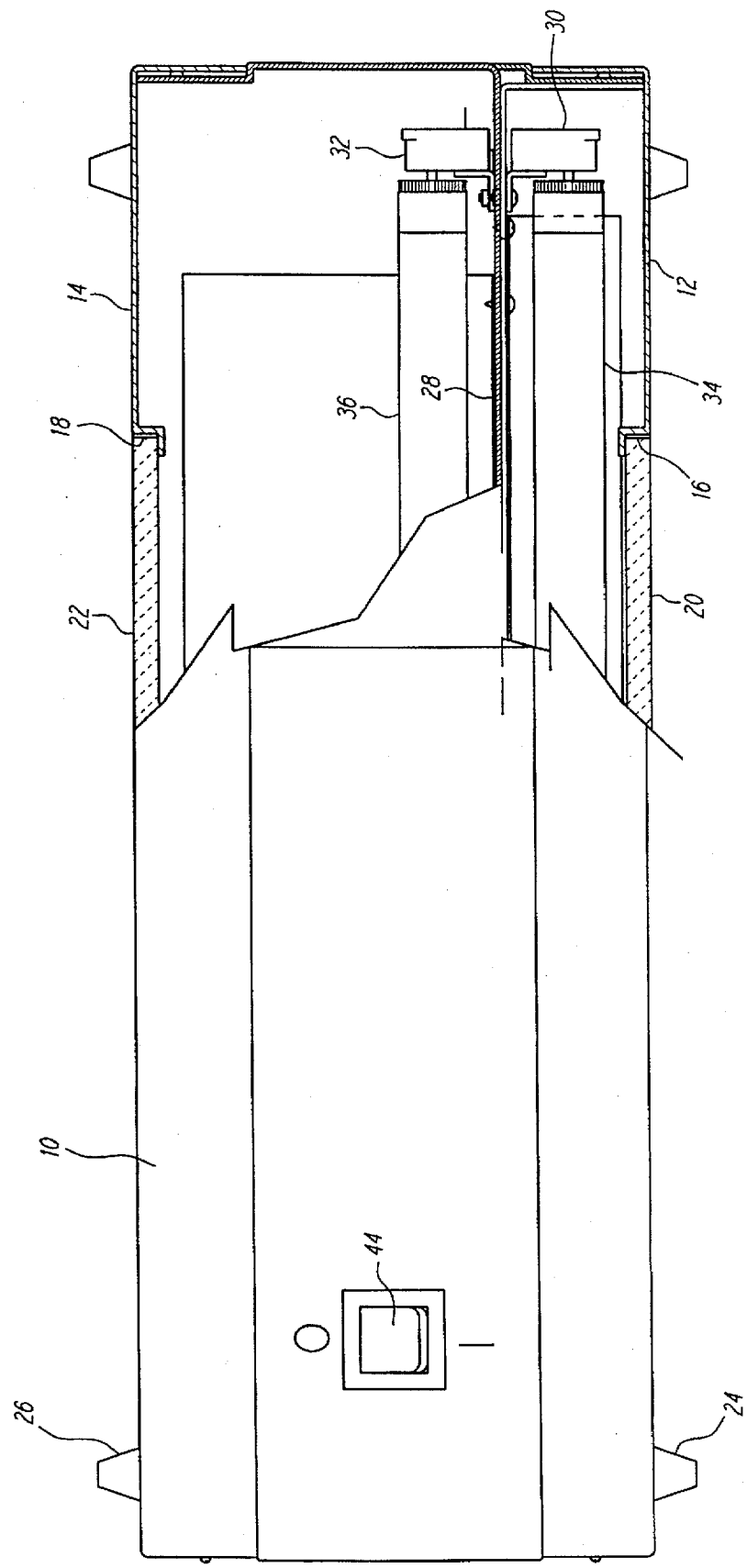
FIG. 2 is a side view with the wall of the housing partially removed of the transilluminator.
Figure 3:
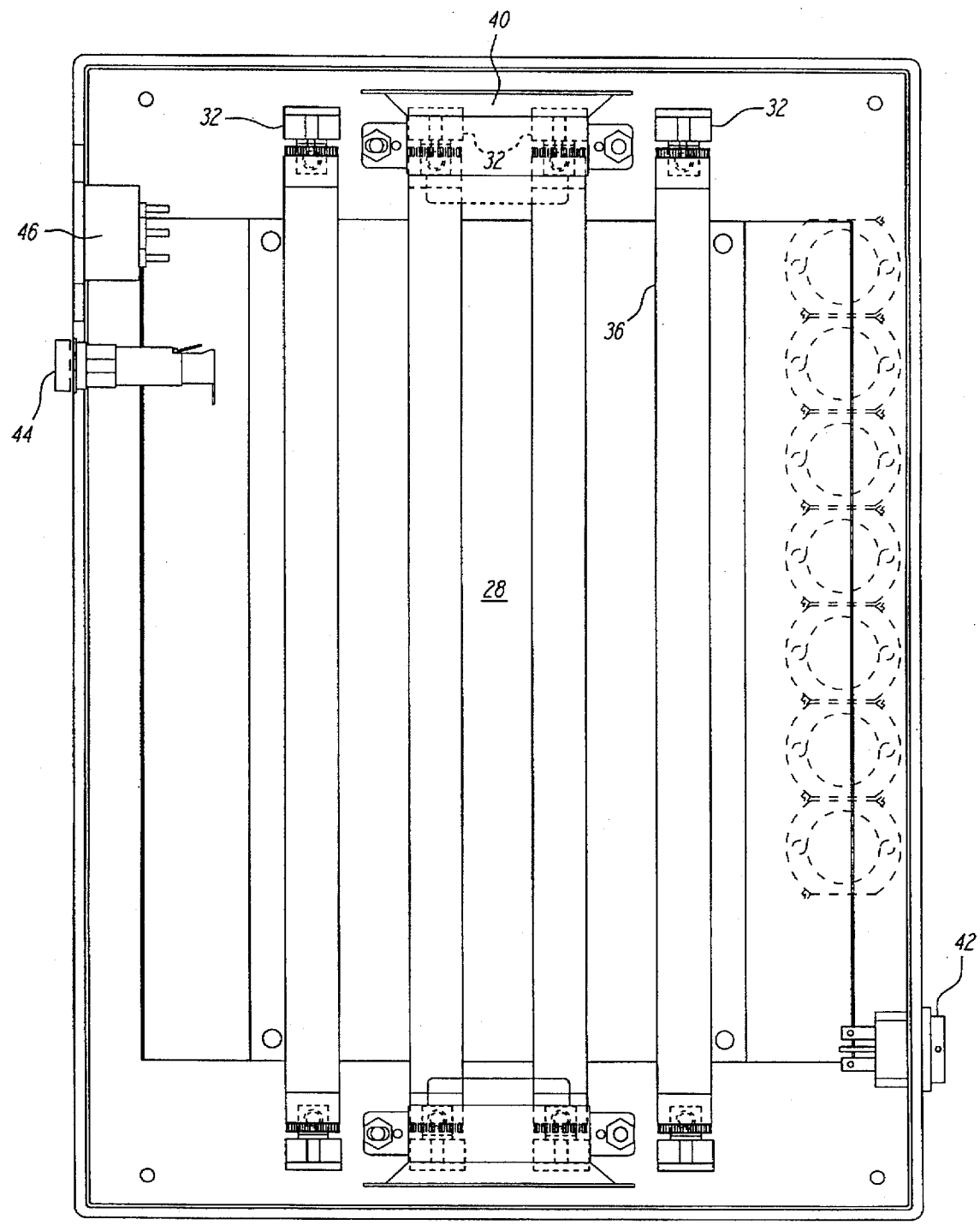
FIG. 3 is a plane view of the first of two opposed sides of the transilluminator taken with that side of the housing removed.
Figure 4:
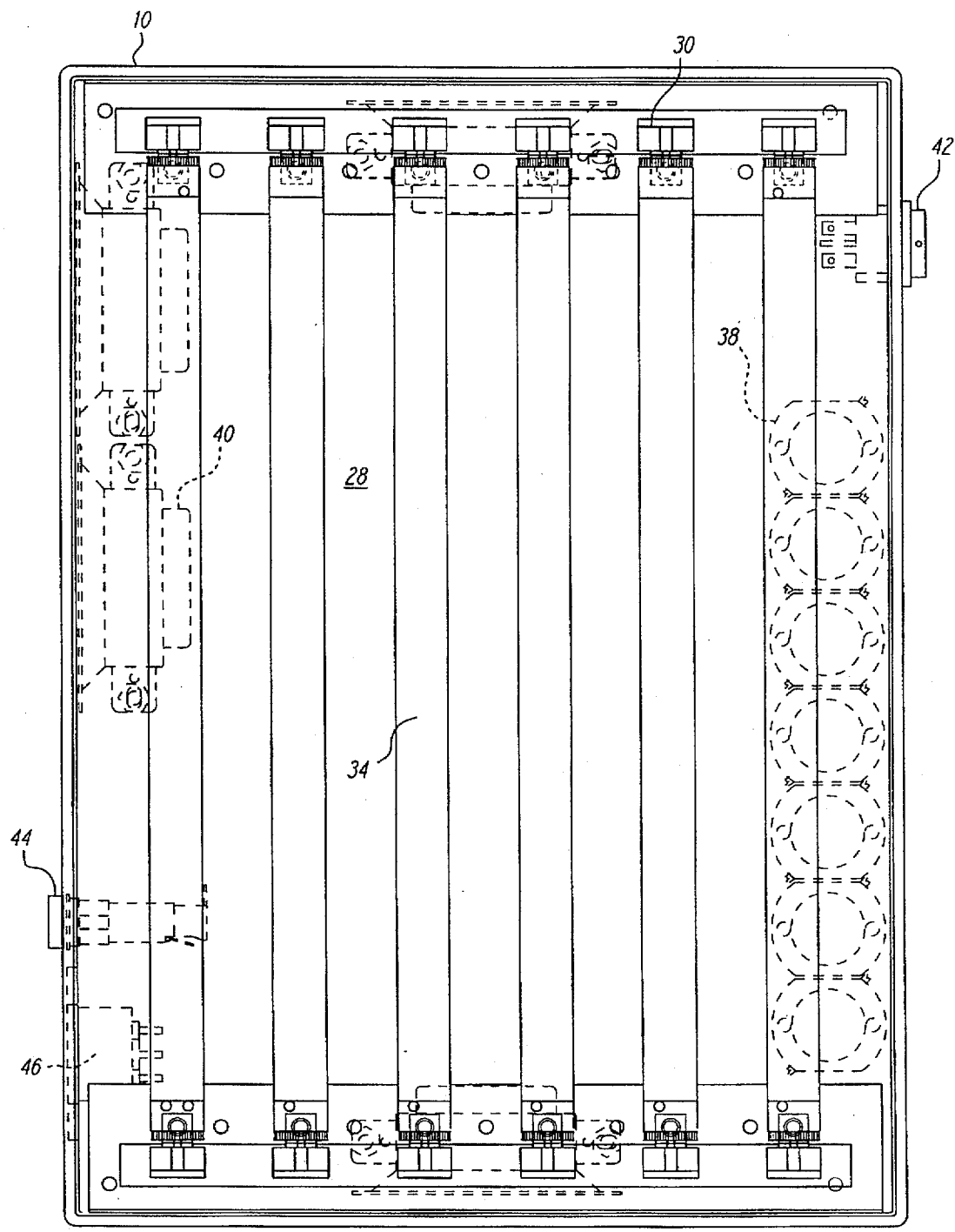
FIG. 4 is a plan view of the second of two opposed sides of the transilluminator taken with that side of the housing removed.

Turning in detail to the drawings, a housing 10, conveniently of sheet metal, provides a complete enclosure with two opposed sides 12 and 14 having windows 16 and 18 for radiation of selected light spectra. The housing 10 includes four other walls spanning between the periphery of each of the opposed sides 12 and 14 to complete the closure.

Each window 16 and 18 includes a lens 20 and 22, respectively. The lenses 20 and 22 may provide diffusion, spectra filtering or other function to prepare the radiated light for the intended use.

The housing 10 includes mounts associated with each of the opposed sides 12 and 14. A first set of four mounts 24 are located on the first of the opposed sides 12 to stably support the housing on a planar surface. A similar set of four mounts 26 are positioned on the opposed side 14 in a similar manner and for the same purpose. Thus, the sets of mounts 24 and 26 provide for a convenient positioning of the housing 10 with either of the windows 20 and 22 facing upwardly to provide a light box of the appropriate spectrum. Other mounts may be employed. A frame around each of the lenses 20 and 22 which extend outwardly beyond both the lenses and the surrounding housing 10 can provide appropriate support. Such a frame could also act to retain water or other fluids spilled on the lens from flowing out and into the housing 10.

Figure 5:
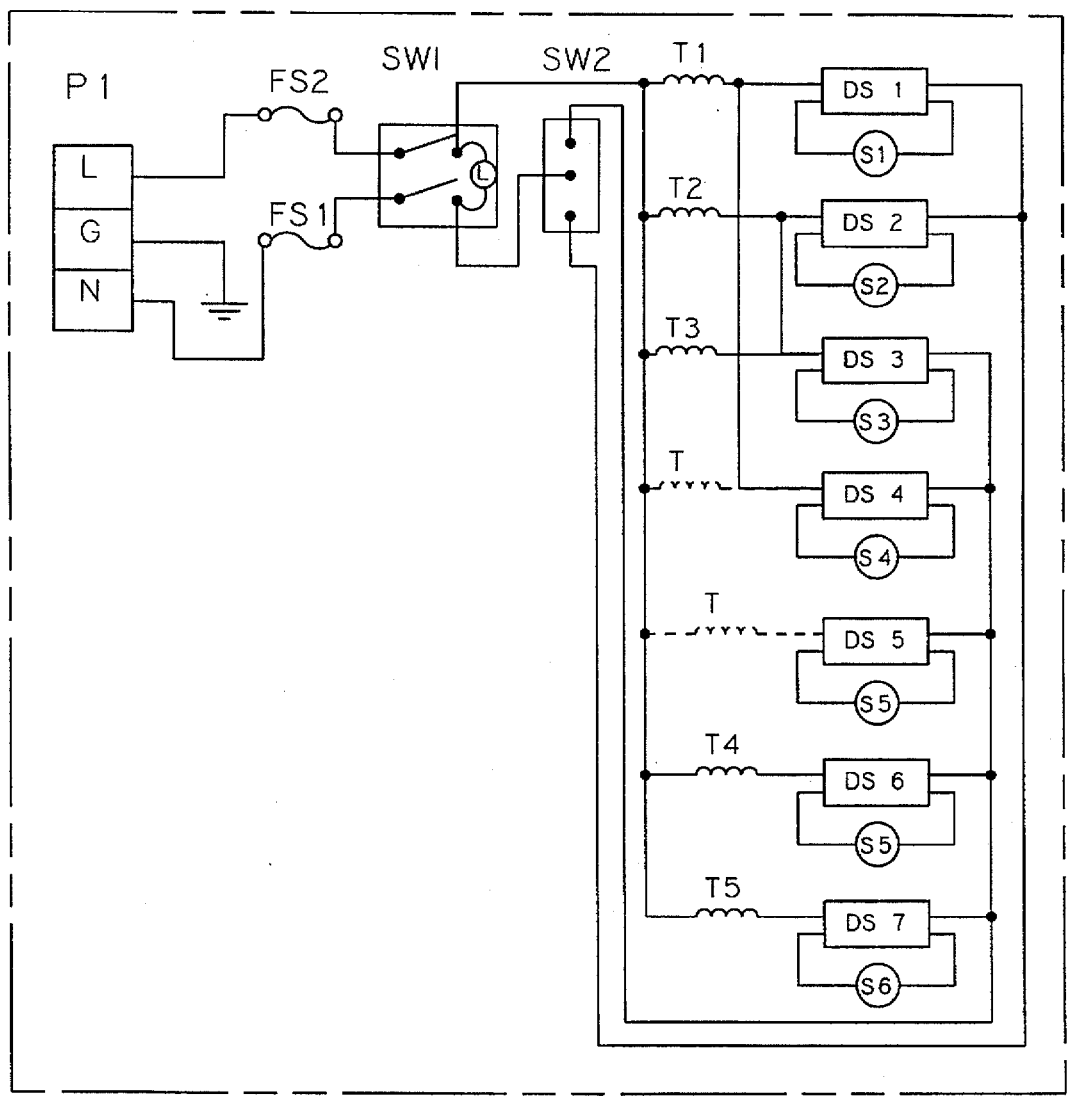
FIG. 5 is a schematic circuit diagram of the transilluminator.

Within the housing 10, a light source is positioned to radiate light of selected spectra through the lenses 20 and 22. A reflector 28 forms part of the light source, extending across the interior of the housing 10 to reflect light toward the windows 16 and 18. The reflector 28 also serves to divide the interior of the housing into two lamp cavities and to mount, on either side of the reflector 28, lampholders 30 and 32. Illustrated in this preferred embodiment are four sets of lampholders 30 and six sets of lampholders 32. In FIG. 5, two sets and five sets are illustrated for simplicity and as another possible configuration.

Lamps 34 and 36, identified as DS in FIG. 5, are mounted in the lampholders 30 and 32, respectively. These lamps 34 and 36 are arranged in parallel with the lenses 20 and 22. It may be recognized that more or less lamps 34 and 36 may be provided. The light source including the reflector 28 with the lamps 34 and 36 may be positioned within the housing 10 substantially parallel to the opposed sides 12 and 14 and may be closer to one than the other depending on optical requirements. When more lamps are used, the lamps can be close to the lens and still achieve good uniformity of light intensity. With fewer light sources, greater spacing from the lens allows for uniform intensity. To decrease the profile of the housing 10 in the present case, several lamps on either side of the reflector have been used. The lamps 34 and 36 may be of any type to generate the spectra of selected interest. In a selected preferred embodiment, the lamps 36 may generate an ultraviolet wavelength through the lens 22. The wavelength generated may selected from the 254 nm, the 302 nm and the 365 nm ranges. With more lamps 36, multiple range capabilities may be realized. Reference is again made to U.S. Pat. No. 5,387,801 which shows one such configuration. The lens 22 in this instance is a filter which filters out all visible light with the usual exception of low 400 nm wavelenths which give a blue glow. Ultraviolet is transmitted by such lenses. The lamps 34 generate a white light through the lens 20 which is preferably a diffuser. Other arrangements are also contemplated such as multiple lenses 20 or 22 on one or both opposed sides 12 and 14 to provide multiple choices of selected electromagnetic radiation appropriately conditioned on each side of the housing 10.

Also positioned within the housing 10 are starters 38, identified as S in FIG. 5, ballasts 42, identified as T in FIG. 5, fuses identified as FS in FIG. 5, and a plug identified as P in FIG. 5. The ballast system preferably is a commercially available system including an iron core ballast, a 12 volt inverter, an electronic chip and an electronic ballast. The conductors as illustrated in FIG. 5 create two circuits, one associated with each set of lamps 34 and 36. A common ON/OFF switch 44, SW1 in FIG. 5, associated with both circuits closes the circuits simultaneously. A gravity switch in the form of a mercury switch 46, SW2 in FIG. 5, is also interposed in both circuits. The switch 46 is mounted to the housing 10 and alternatively energizes one circuit or the other depending on the orientation of the housing 10. Thus, with the switch 44 on, placement of the housing 10 on the first set of four mounts 24 results in the mercury switch 46 taking the position that the lamps 36 are on while the lamps 34 are off. Inverting the housing 10 such that the second set of four mounts 26 rests on a planar surface causes the opposite to occur. Instead or in addition, a selector switch 48 may be used. This switch would disable one or the other of the circuits.

Accordingly, an improved, convenient transilluminator is disclosed. While embodiments and applications of this invention have been shown and described, it would be apparent to those skilled in the art that many more modifications are possible without departing from the inventive concepts herein. The invention, therefore is not to be restricted except in the spirit of the appended claims.

What is claimed is:

1. A multiple wavelength light source comprising
   a housing having two opposed sides and defining an enclosure;
   a first window through a first of the opposed sides having a first lens;
   a second window through a second of the opposed sides having a second lens;
   a light source within the housing having lamps each positioned to radiate light toward at least one of the first lens and the second lens, the first lens and the second lens in combination with the lamps radiating light of different selected spectra from each when the lamps are energized;
   a first mounting on the first of the opposed sides to stably support the housing on a planar surface with the second of the opposed sides facing upwardly;
   a second mounting on the second of the opposed sides to stably support the housing on a planar surface with the first of the opposed sides facing upwardly.

2. The multiple wavelength light source of claim 1 further comprising
   the lamps including first lamps positioned to radiate light toward the first lens and second lamps positioned to radiate light toward the second lens;
   a first circuit selectively energizing the first lamps;
   a second circuit selectively energizing the second lamps, the first circuit and the second circuit jointly including a gravity switch mounted to move with the housing to alternatively open the first circuit and the second circuit.

3. The multiple wavelength light source of claim 2, there being a reflector between the first lamps and the second lamps.

4. The multiple wavelength light source of claim 2, the gravity switch being a mercury switch.

5. The multiple wavelength light source of claim 2, the first circuit and the second circuit jointly further including an ON/OFF switch selectively closing both the first circuit and the second circuit simultaneously.

6. A multiple wavelength light source comprising
   a housing having two opposed sides and defining an enclosure;
   a first window through a first of the opposed sides having a first lens;
   a second window through a second of the opposed sides having a second lens;
   a light source within the housing having lamps each positioned to radiate light toward at least one of the first lens and the second lens, the first lens and the second lens in combination with the lamps radiating light of different selected spectra from each when the lamps are energized, the first lens and the second lens in combination with the lamps radiating light of a first selected spectra of ultraviolet light from the first lens and a second selected spectra of light different from the first selected spectra of ultraviolet light from the second lens when the lamps are energized;
   a first mounting on the first of the opposed sides to stably support the housing on a planar surface with the second of the opposed sides facing upwardly;

a second mounting on the second of the opposed sides to stably support the housing on a planar surface with the first of the opposed sides facing upwardly.

7. The multiple wavelength light source of claim 6, the second selected spectra of light being visible light.

8. The multiple wavelength light source of claim 7, the visible light being white light.

9. A multiple wavelength light source comprising a housing having two opposed sides and defining an enclosure;

a first window through a first of the opposed sides having a first lens;

a second window through a second of the opposed sides having a second lens;

a light source within the housing having first lamps positioned to radiate light toward the first lens and second lamps positioned to radiate light toward the second lens;

a first circuit selectively energizing the first lamps;

a second circuit selectively energizing the second lamps, the first circuit and the second circuit jointly including a gravity switch mounted to move with the housing to alternatively open the first circuit and the second circuit, the first lens in combination with the first lamps radiating light of a first selected spectra of ultraviolet light from the first lens when the first lamps are energized and the second lens in combination with the second lamps radiating light of a second selected spectra of light different from the first selected spectra of ultraviolet light from the second lens when the second lamps are energized.

10. The multiple wavelength light source of claim 9, the second selected spectra of light being visible light.

11. The multiple wavelength light source of claim 10, the visible light being white light.

12. A multiple wavelength light source for transilluminating, comprising a housing having two opposed sides and defining an enclosure;

a first window through a first of the opposed sides having a first lens;

a second window through a second of the opposed sides having a second lens;

a light source within the housing having first lamps positioned to radiate light toward the first lens and second lamps positioned to radiate light toward the second lens, the first lens in combination with the first lamps radiating light of a first selected spectra of ultraviolet light from the first lens when the first lamps are energized and the second lens in combination with the second lamps radiating white light from the second lens when the second lamps are energized.

13. The multiple wavelength light source of claim 12 further comprising a first circuit selectively energizing the first lamps;

a second circuit selectively energizing the second lamps, the first circuit and the second circuit jointly including a mercury switch mounted to move with the housing to alternatively open the first circuit and the second circuit;

first mounts on the first of the opposed sides to stably support the housing on a planar surface with the second of the opposed sides facing upwardly;

second mounts on the second of the opposed sides to stably support the housing on a planar surface with the first of the opposed sides facing upwardly.

14. The multiple wavelength light source of claim 13, the first circuit and the second circuit jointly further including an ON/OFF switch selectively closing both the first circuit and the second circuit simultaneously.

* * * * *